United States Patent [19]

Pommer et al.

[11] 4,042,686
[45] Aug. 16, 1977

[54] FUNGICIDAL COMPOSITIONS

[75] Inventors: Ernst-Heinrich Pommer, Limburgerhof; Rudolf Polster, Frankenthal; Friedrich Loecher, Limburgerhof, all of Germany

[73] Assignee: BASF Aktiengesellschaft, Ludwigshafen, Germany

[21] Appl. No.: 676,571

[22] Filed: Apr. 13, 1976

[30] Foreign Application Priority Data

May 14, 1975 Germany .............................. 2521405

[51] Int. Cl.$^2$ ...................... A01N 13/00; A01N 9/20; A01N 9/24
[52] U.S. Cl. ..................................... 424/164; 424/309
[58] Field of Search ............................... 424/164, 309

[56] References Cited

U.S. PATENT DOCUMENTS 1,652,339  12/1927  Zernik ................................. 424/164

FOREIGN PATENT DOCUMENTS 1,218,792  10/1964  Germany ............................ 424/309

OTHER PUBLICATIONS

Chem. Week, July 26, 1972, p. 43.

Primary Examiner—Albert T. Meyers
Assistant Examiner—D. W. Robinson
Attorney, Agent, or Firm—Keil, Thompson & Shurtleff

[57] ABSTRACT

A synergistic fungicidal composition consisting essentially of
a. wettable sulfur and
b. diisopropyl 3-nitroisophthalate, the weight ratio of a:b being from 2:1 to 5:1.

4 Claims, No Drawings

FUNGICIDAL COMPOSITIONS

The present invention relates to a fungicide containing a mixture of two active ingredients.

It is known to use sulfur in the form of a finely divided wettable formulation known as wettable sulfur (Chemical Week, July 26, 1972, page 43), and diisopropyl 3-nitroisophthalate (German 1,218,792), as fungicides for combatting fungi.

We have now found that a fungicide containing a composition of
a. wettable sulfur and
b. diisopropyl 3-nitroisophthalate
has a fungicidal action on fungi, especially plant-pathogenic fungi, which is far superior to that of its individual ingredients.

The fungicides of the invention are suitable in general for combatting plant diseases caused by fungi, especially mildews or Fusarium species in cereals, and *Rhizoctonia solani*.

The weight ratio of the active ingredients at which synergism occurs varies widely; the preferred ratio range of a:b is from 2:1 to 5:1, especially 3:1.

Application may be effected for instance in the form of powders, suspensions, dispersions, emulsions, oil dispersions, pastes, dusts or broadcasting agents by spraying, atomizing, dusting, broadcasting or watering. The forms of application depend entirely on the purpose for which the agents are being used; in any case they should ensure a fine distribution of the active ingredient.

For the preparation of emulsions, pastes and oil dispersions, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol, polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dust and broadcasting agents may be prepared by mixing or grinding the active ingredients with a solid carrier.

The formulations contain from 0.1 to 95% and preferably 0.5 to 90% by weight of active ingredient.

There may be added to the compositions oils of various types, herbicides, fungicides, nematocides, insecticides, bactericides, trace elements, fertilizers, antifoams (e.g., silicones) and growth regulators.

When the compositions of the invention are used for treating plants, application rates are from 0.5 to 6 kg/ha.

EXAMPLE 1

The active ingredients and compositions thereof in the amounts (% by weight) given in the table are uniformly distributed in a still liquid malt nutrient agar. The agar is then poured into flat glass dishes having a diameter of 8 cm. After the agar has solidified, it is centrally inoculated with 48- hour-old mycelium of snow mold (*Fusarium nivale*). The dishes are incubated at 25° C. After 5 days the spread of the fungus colony is assessed and the action (inhibition) of the fungicides and fungicidal composition is determined.

TABLE 1

| Active ingredient | Weight ratio a:b | Wt% of active ingredient in nutrient agar | Diameter of fungus colony in mm | Action | Sum of actions of a) 0.1 + b) 0.05 17 + 9 = 26 |
|---|---|---|---|---|---|
| Untreated | — | — | 60 = 100 | 0 | |
| a) Wettable sulfur | — | 0.05 | 57 = 95% | 5 | |
| | | 0.1 | 50 = 83% | 17 | |
| b) Diisopropyl-3-nitroisophthalate | — | 0.05 | 55 = 91% | 9 | |
| | | 0.1 | 47 = 78% | 22 | |
| Composition of a and b | 2:1 | 0.067 + 0.033 | 32 = 53% | 47 | 26 |
| | 3:1 | 0.075 + 0.025 | 35 = 58% | 42 | 26 |
| | 4:1 | 0.08 + 0.02 | 35 = 58% | 42 | 26 |
| | 5:1 | 0.083 + 0.017 | 38 = 63% | 37 | 26 |

EXAMPLE 2

A further experiment is carried out in the same manner as in Example 1 with *Fusarium culmorum*, a fungus occurring in cereals.

TABLE 2

| Active ingredient | Weight ratio a:b | Wt% of active ingredient in nutrient agar | Diameter of fungus colony in mm | Action | Sum of action of a) 0.1 + b) 0.05 16 + 29 = 45 a) 0.1 + b) 0.025 16 + 15 (estimated) = 31 |
|---|---|---|---|---|---|
| Untreated | — | — | 77 = 100 | 0 | |
| a) Wettable sulfur | — | 0.05 | 75 = 975% | 3 | |
| | | 0.1 | 65 = 84% | 16 | |
| b) Diisopropyl-3-nitroisophthalate | — | 0.05 | 55 = 71% | 29 | |
| | | 0.1 | 45 = 58% | 42 | |
| Composition of a and b | 2:1 | 0.067 + 0.033 | 37 = 48% | 52 | 45 |
| | 3:1 | 0.075 + 0.025 | 35 = 45% | 55 | 45 |
| | 4:1 | 0.08 + 0.02 | 35 = 45% | 55 | 45 |
| | 5:1 | 0.083 + 0.017 | 40 = 52% | 48 | 31 |

We claim:

1. A synergistic fungicidal composition consisting essentially of
   a. wettable sulfur and
   b. diisopropyl 3-nitroisophthalate, the weight ratio of a:b being from 2:1 to 5:1.

2. A process for combatting plant-pathogenic fungi which comprises applying to the plants a fungitoxic amount of a composition consisting essentially of
   a. wettable sulfur and
   b. diisopropyl 3-nitroisophthalate, the weight ratio of a:b being from 2:1 to 5:1.

3. A composition as claimed in claim 1 wherein the weight ratio of a:b is approximately 3:1.

4. A process as claimed in claim 2 wherein the weight ratio of a:b is approximately 3:1.

* * * * *